US 6,579,521 B2
Jun. 17, 2003

(54) METHODS OF THERAPY FOR HIV INFECTION

(75) Inventor: David Sahner, Berkeley, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/974,470

(22) Filed: Oct. 9, 2001

(65) Prior Publication Data

US 2002/0048748 A1 Apr. 25, 2002

Related U.S. Application Data

(60) Provisional application No. 60/242,090, filed on Oct. 20, 2000.

(51) Int. Cl.⁷ .............................................. A61K 45/05
(52) U.S. Cl. ......................... 424/85.2; 514/49; 514/50; 514/252.1; 514/255.01; 514/256; 514/934
(58) Field of Search .............................. 424/153.1, 85.1; 514/49, 50, 252.1, 255.01, 256, 934

(56) References Cited

U.S. PATENT DOCUMENTS

| 5,419,900 A | 5/1995 | Lane et al. |
| 5,969,079 A | 10/1999 | Lubowitz et al. |
| 2002/0048584 A1 * | 4/2002 | Pomerantz ............... 424/153.1 |

FOREIGN PATENT DOCUMENTS

| WO | WO 99/26658 | 6/1999 |
| WO | WO 99/48526 | 9/1999 |

OTHER PUBLICATIONS

Pahwa et al., "Interleukin–2 therapy in HIV infection", AIDS Patient Care and STDS, vol. 12, No. 3(Mar. 1998), pp. 187–197.*

Wodarz et al. "Specific therapy regimes could lead to long-term immunological control of HIV", Proceedings of the National Acadamy of Sciences, vol. 96, No. 25(Dec. 7, 1999), pp. 14464–9.*

Arno et al. "Efficacy of low-dose subcutaneous interleukin–2 to treat advanced human immunodeficiency virus type 1 in persons with </=250/microL CD4 T cells and undetectable plasma virus load", Journal of Infectious Diseases, vol. 180, No. 1(Jul. 1999) pp. 56–60.*

Hengge et al. "Randomized, controlled phase II trial of subcutaneous interleukin–2 in combination with highly active antiretroviral therapy (HAART) in HIV patients", AIDS, vol. 12, No. 17, (Dec. 3, 1998), pp. F225–34.*

Alvarado-Diez, R., et al., "Interleukin 2 Plus HAART Does Not Increase the Viral Load," XIII International AIDS Conference, 2000, Abstract No. WePeA4086.

Arendt, P., et al., IL–2 in Patients with Low CD4 and Resistant Virus: Efficacy and Cytokine (CK)/Chemokine (ChK) Profiles, XIII International AIDS Conference, 2000, Abstract No. ThPeB5033.

Carpenter, C., et al., "Antiretroviral Therapy in Adults," JAMA, 2000, pp. 381–391, vol. 283(3).

Davey, R., et al., "HIV–1 and T Cell Dynamics After Interruption of Highly Active Antiretroviral Therapy (HAART) in Patients with a History of Sustained Viral Suppression," PNAS, 1999, pp. 15109–15114, vol. 96(26).

Emert, R., et al., "Structured Antiviral Treatment Interruption Followed by Daily Low Dose Interleukin 2 (IL–2) Reveals Immune Response to HIV," XIII International AIDS Conference, 2000, Abstract No. WePeB4285.

Fisher, M., et al., "Randomized Study of Intermittent Subcutaneous Interleukin–2 (IL–2) Therapy Without Anti-Retrovirals Versus No Treatment," XIII International AIDS Conference, 2000, Abstract No. LbOr28.

Hecht, F., et al., "A Randomized Trial of IL–2 Added to HAART for Primary HIV Infection," XIII International AIDS Conference, 2000, Abstract No. WeOrB541.

Levy, Y., et al., "Long Term (3 Years) Efficacy of IL2 Therapy in HIV–Infected Patients. Results of the Follow-up of the Randomized ANRS 048 Trial," XIII International AIDS Conference, 2000, Abstract No. ThPeB5032.

Malnati, M., et al., "Retrospective Analysis of HHV–8 Plasma Viremia and Cellular Viral Load in a Cohort of HIV–Seropositive Individuals Receiving HAART + IL–2," XIII International AIDS Conference, 2000, Abstract No.WePeA4009.

Oliva, A., et al., "Effects of In Vivo IL–2 Administration on InVitro CC–Chemokine Production and Viral Isolation in HIV–Infected Individuals Receiving HAART," XIII International AIDS Conference, 2000, Abstract No.WeOrB490.

Ostrowski, M., et al., "The Role of CD4+ T Cell Help and CD40 Ligand in the Expansion of HIV–Specific Memory Cytotoxic CD8+ T Cell Responses," XIII International AIDS Conference, 2000, Abstract No. TuPeA3040.

Ruiz, L., et al., "Structured Treatment Interruption in Chronically HIV–1 Infected Patients After Long-Term Suppression," AIDS, 2000, pp. 397–403, vol. 14(4).

(List continued on next page.)

Primary Examiner—Jeffrey Stucker
(74) Attorney, Agent, or Firm—W. Murray Spruill; Charlene A. Launer; Robert P. Blackburn

(57) ABSTRACT

Methods for promoting immunologic control of human immunodeficiency virus (HIV) in an HIV-infected subject are provided. The methods comprise administering to the subject highly active antiretroviral therapy (HAART) for at least one cycle of an intermittent dosing regimen in combination with administration of a pharmaceutical composition comprising a therapeutically effective amount of interleukin-2 (IL-2) or variant thereof. The combination of daily or intermittent administration of IL-2 (or variant thereof) and intermittent HAART promotes immunologic control of viral replication in the absence of HAART, thereby prolonging the length of time a patient may discontinue HAART before viral rebound necessitates further administration of HAART. Administration of IL-2 therapy in combination with an intermittent HAART dosing regimen provides an effective method for treating a subject infected with HIV.

37 Claims, No Drawings

OTHER PUBLICATIONS

Ruxrungtham, K., "Naïve and Memory Phenotypes of CD4+ T Cells and mRNA Expression of IL-2 in HIV-Infected Thai patients Treated with Various Doses of Subcutaneous (SC) IL-2," *XIII International AIDS Conference*, 2000, Abstract No. ThPpB1481.

Umscheid, C., et al., "HIV Envelope Induces Virus Expression in the HIV-Infected Resting CD4+ T Cell Reservoir without Inducing Cellular Activation Orapoptosis," *XIII International AIDS Conference*, 2000, Abstract LbPeA7024.

Yoder, C., et al., A Randomized Controlled Trial of Intermittent Versus Continuous Highly Active Antiretroviral Therapy (HAART), *XIII International AIDS Conference*, 2000, Abstract No. LbOr11.

Yoder, C., et al., "Short Cycle Intermittent HAART: A Pilot Study," *XIII International AIDS Conference*, 2000, Abstract No. LbOr12.

* cited by examiner

METHODS OF THERAPY FOR HIV INFECTION

CROSS-REFERENCE TO RELATED APPLICATION

This application claims benefit of U.S. Provisional No. 60/242,090 filed Oct. 20, 2000, which is herein incorporated by reference in its entirety.

FIELD OF THE INVENTION

The present invention is directed to methods of therapy for human immunodeficiency virus (HIV) infection, more particularly to the use of intermittent antiretroviral therapy in combination with interleukin-2 (IL-2) to promote long-lasting immunologic control of HIV.

BACKGROUND OF THE INVENTION

Infection with the human immunodeficiency virus (HIV) results in progressive deterioration of the immune system in most infected subjects. During disease progression, key cells associated with the immune system become infected with HIV, including, e.g., CD4+ T cells, macrophages/monocytes, and glial cells. Prolonged HIV infection frequently culminates in the development of AIDS. In the late stages of this disease, the immune system is severely compromised due to loss or dysfunction of CD4+ T cells (Shearer et al. (1991) AIDS 5:245–253).

HIV-1-specific CD8+ cytotoxic T lymphocytes appear to be critical in the immunologic control of HIV-1 soon after the acquisition of infection. CTL precursors specific for cells expressing several HIV-1 gene products, including Gag, Pol, and Env antigens, are detectable within three weeks of the primary infection syndrome (Koup et al. (1994) J. Virol. 68:4650–4655). Since CTL activity is antigen driven, the waning in responding T-cell subsets that generally occurs with the passage of time is not unexpected. The clinical significance of this cellular immune response to HIV has been demonstrated in a number of studies, and impairment of this response appears to be associated with more rapid disease progression. Lymphokines elaborated by HIV-specific CD4+ T-cells are critical in supporting the genesis of these mature cytotoxic T lymphocytes directed against HIV-1 (Rosenberg et al. (1997) Science 278:1447–1450), lending credence to the notion that virus-specific T-helper cells are necessary for maintenance of effective immunity to HIV.

Anti-retroviral drugs, such as reverse transcriptase inhibitors, viral protease inhibitors, and viral entry inhibitors, have been used to treat HIV infection (Caliendo et al. (1994) Clin. Infect. Dis. 18:516–524). More recently, treatment with combinations of these agents, known as highly active antiretroviral therapy (HAART), has been used to effectively suppress replication of HIV (Gulick et al. (1997) N. Engl. J. Med. 337:734–9 (see comments); Hammer et al. (1997) N. Engl. J. Med. 337:725–733). However, HAART is primarily efficacious with regard to the prevention of the spread of infection into uninfected cells. This therapy cannot efficiently reduce the residual, latent proviral DNA integrated into the host cellular genome (Wong et al. (1997) Science 278:1291–1295 (see comments); Finzi et al. (1997) Science 278:1295–1300 (see comments); Finzi et al. (1999) Nat. Med. 5:512–517; Zhang et al. (1999) N. Engl. J. Med. 340:1605–1613).

Anecdotal reports of individuals who have discontinued HAART have revealed a rapid relapse of viremia, most often within a few weeks of ceasing anti-viral therapy (Ruiz et al. (2000) AIDS 14:397–403). Consequently, HAART must be administered indefinitely to prevent reactivation of latent virus. Continuous treatment with HAART is problematic, as HAART regimens are expensive, are difficult to comply with, and have many side effects. In addition, prolonged treatment with antiretroviral agents often leads to the emergence of drug resistant viral strains (Larder et al. (1989) Science 246:1155–1158; Kellam et al. (1992) Proc. Natl. Acad. Sci. USA 89:1934–1938; St. Clair et al. (1991) Science 253:1557–1559). The emergence of drug-resistant viral strains is delayed with combination treatment aimed at different points in the HIV replication cycle (D'Aquila (1994) Clin. Lab. Med. 14:393–422). However, a significant portion of patients treated with combination therapy may eventually harbor strains of HIV having multi-drug resistance (Schinazi et al. (1994) Int. Antiviral News 2:72–5).

Recombinant human interleukin-2 (IL-2) has been studied in the setting of HIV disease for over a decade. This immunobiologic agent, when administered intermittently by either the SC or CIV route in conjunction with antiretroviral therapy, produces prominent and sustained increases in the CD4+ T-cell count in the vast majority of HIV-infected patients who have been recently studied (Kovacs et al. (1996) N. Engl. J. Med. 335:1350–1356; Davey et al. Abstract 689, ICAAC (San Francisco, Calif.), September, 1999; Arno et al. (1999) JID 180:56–60; Carr et al. (1998) J. Infect. Dis. 178(4):992–999; Hengge et al. (1998) AIDS 12:F225–F234; Levy et al. (1999) Lancet 353:1923–1929). The increase in the CD4+ T-cell compartment is polyclonal and is characterized by the genesis of CD4+ T-cells that are functional in vitro (Levy et al. (1999) Lancet 353:1923–1929).

Intermittent cycles of IL-2 produce transient rises in plasma viral load in some HIV-infected subjects (Davey et al. (1997) J. Infect. Dis. 175:781–789), however no controlled trials have demonstrated a deleterious long-term effect on viral burden. Indeed, several recent studies indicate IL-2 might have an antiviral effect (Davey et al. (1999) J. Infect. Dis. 179:849–858). The reason an antiviral effect of IL-2 has been observed only in several recent studies might relate to the higher sensitivity of the assays employed and/or the use of HAART.

In vitro data have shown that the IL-2 responsiveness of CD4+ cells of subjects well controlled virologically on HAART is greater than that of cells culled from patients with suboptimal virologic control. However, cessation of HAART in patients receiving cycles of IL-2 therapy in the past frequently leads to virologic rebound (Davey et al. (1999) Abstract 689, ICAAC (San Francisco, Calif.), September, 1999).

Given the problems associated with prolonged treatment with HAART and the tendency for rapid viral rebound following cessation of this combination therapy, even in patients receiving IL-2 therapy in the past, better methods are needed to achieve longterm immunologic control of HIV.

SUMMARY OF THE INVENTION

Methods for promoting immunologic control of the human immunodeficiency virus (HIV) in an HIV-infected subject are provided. The methods comprise administering to the HIV-infected subject an antiviral therapy selected from highly active antiretroviral therapy (HAART) or dual protease inhibitor therapy for at least one cycle of an intermittent dosing regimen in combination with administration of a pharmaceutical composition comprising a therapeutically effective amount of interleukin-2 (IL-2) or variant thereof. HAART comprises daily administration of therapeutically effective amounts of at least three antiretroviral agents. An intermittent HAART dosing regimen comprises administering HAART until plasma viral RNA is undetectable in the patient and then discontinuing administration of HAART until plasma viral RNA reaches an acceptable threshold level in the patient. Therapeutically effective doses of IL-2 or variant thereof are administered daily or intermittently during each cycle of an intermittent HAART or other antiviral dosing regimen. The combination of daily or intermittent administration of IL-2 (or variant thereof) and intermittent HAART promotes immunologic control of viral replication, thereby prolonging the length of time a patient may discontinue HAART before viral rebound necessitates further administration of HAART. Administration of IL-2 therapy in combination with an intermittent HAART dosing regimen provides an effective method for treating a subject infected with HIV.

DETAILED DESCRIPTION OF THE INVENTION

The present invention relates to methods of promoting immunologic control of human immunodeficiency virus (HIV), more particularly HIV-1, in an HIV-infected patient. By "immunologic control" is intended the ability of an HIV-infected patient to effectively mount a cellular immune defense against actively replicating HIV in the absence of antiretroviral agents. For purposes of the present invention, such immunologic control is manifested in the form of increased anti-viral immune reactivity to actively replicating HIV. By "anti-viral immune reactivity" is intended proliferative expansion of antigen-selected lymphocytes, more particularly the HIV antigen-specific CD8+ subset of T cells, in response to an increase in viral load, such as that seen with discontinuance of antiretroviral therapy. Proliferative expansion of CD8+ T cells, particularly HIV antigen-specific CD8+ T cells, effectively leads to a subsequent decline in viral load, such that the population of actively replicating virus is maintained below an acceptable threshold level as defined elsewhere herein. The methods of the invention are useful in the treatment of HIV-infected individuals.

Methods of the invention comprise administering to an HIV-infected subject an antiviral therapy for at least one cycle of an intermittent dosing regimen in combination with administration of a pharmaceutical composition comprising a therapeutically effective amount of interleukin-2 (IL-2) or variant thereof. By "antiviral therapy" is intended highly active antiretroviral therapy (HAART) or dual protease inhibitor therapy. While the methods of the invention are discussed more fully in terms of HAART, it is recognized that the methods are intended to cover dual protease inhibitor therapy as well. HAART is administered to deplete the population of actively replicating HIV, preferably to an undetectable level, in the HIV-infected subject. IL-2 is administered to maintain a background level of this lymphokine within the HIV-infected patient, with the background level being sufficient to stimulate the immune system, thereby providing for immune reconstitution in the treated patient. An intermittent dosing regimen allows for an HIV-infected subject to have a time period off of HAART, which is beneficial given the expense, complicated regimen, and undesirable long-term side effects associated with continuous HAART. By subjecting an HIV-infected patient to periods on and off HAART, the population of actively replicating HIV virus is allowed to fluctuate between an undetectable level and an acceptable threshold level. During periods of discontinuance of HAART, there is a burst of replicating HIV. However, because the patient is immune reconstituted prior to discontinuance of HAART as a result of IL-2 therapy, an effective immunologic response can be mounted against the replicating virus, thereby returning viremia to within an acceptable threshold level, if not permanently, then for a prolonged period of time. For purposes of the present invention, this ability to return viremia to within an acceptable threshold level is referred to as immunological containment of the virus. Where rebound of actively replicating virus occurs above the acceptable threshold level following a prolonged period of immunological containment, subsequent cycles of intermittent HAART are administered to the patient. The methods of the invention are described in more detail below.

By "HAART" is intended combination therapy with at least three antiretroviral agents, each of which is administered to the subject in a therapeutically effective amount. For purposes of the present invention, antiretroviral agents include any substance that can inhibit, reduce, or eliminate retroviral infection of a cell. A number of these agents are commercially available for administration according to the manufacturer's recommended dosage. Such antiretroviral agents include, but are not limited to, the two classes known as reverse transcriptase inhibitors and protease inhibitors, as well as agents that are inhibitors of viral entry. Although any combination of three or more of these agents can be used, preferably HAART comprises the administration of therapeutically effective amounts of at least one reverse transcriptase inhibitor and at least one protease inhibitor in combination with at least one additional antiretroviral agent. For example, in one embodiment of the invention, at least two reverse transcriptase inhibitors are administered in combination with at least one protease inhibitor. In another embodiment of the invention, at least two protease inhibitors are administered in combination with at least one reverse transcriptase inhibitor.

A number of reverse transcriptase inhibitors are commercially available for use in administering HAART. Examples include, but are not limited to, nucleoside analogs, which are a class of compounds that are known to inhibit HIV, and non-nucleoside drugs. Nucleoside analogs are exemplified by didanosine (2',3'-dideoxyinosine or [ddI], available as Videx® from Bristol Myers-Squibb, Wallingford, Conn.); zidovudine (3'-azido-2',3'-dideoxythymidine or azidothymidine [AZT], available from Glaxo-Wellcome Co., Research Triangle Park, N.C.); zalcitabine (2',3'-dideoxycytidine [ddC], available as Hivid® from Hoffman-La Roche, Basel, Switzerland); lamivudine 2'-deoxy-3'-thiacytidine [3TC] (Epivir®, available from Glaxo-Wellcome Co.); stavudine (2',3'-didehydro-2',3'-dideoxythimidine [D4T] available as Zerit®) from Bristol Myers-Squibb); and the combination drug zidovudine plus lamivudine (Combivir®, available from Glaxo Wellcome). These particular drugs belong to the class of compounds known as 2',3'-dideoxynucleoside analogs, which, with some exceptions such as 2',3'-dideoxyuridine [DDU], are known to inhibit HIV replication, but have not been reported to clear any individual of the virus. Other nucleoside reverse transcriptase inhibitors include abacavir (1592U89, Ziagen™, available from Glaxo-Wellcome Co.). Non-nucleoside reverse transcriptase inhibitors include nevirapine (Viramune™, available from Boehringer Ingelheim Pharmaceuticals, Inc.); delaviridine (Rescriptor®, available from Pharmacia & Upjohn, Kalamazoo, Mich.); and efavirenz (available as Sustiva®, from DuPont Merck).

Examples of protease inhibitors useful in the present invention include, but are not limited to, Indinavir sulfate (available as Crixivan™ capsules from Merck & Co., Inc., West Point, Pa.), saquinavir (Invirase® and Fortovase®, available from Hoffmnan-La Roche), ritonavir (Norvir®, available from Abbott Laboratories, Abbott Park, Ill.); ABT-378 (new name: lopinavir, available from Abbott Laboratories); Amprenavir (Agenerase™, available from Glaxo Wellcome, Inc.); and Nelfinavir (Viracept®), and GW141 (available from Glaxo Wellcome/Vertex).

Such examples of reverse transcriptase and protease inhibitors are not intended to be limiting. It is recognized that any known inhibitor, as well as those under development, may be used in the methods of the invention. See, for example, the drugs for HIV infection disclosed in *Medical Letter* 42(Jan. 10, 2000):1–6, herein incorporated by reference.

Suitable human dosages for these compounds can vary widely. However, such dosages can readily be determined by those of skill in the art. Therapeutically effective amounts of these drugs are administered during HAART. By "therapeutically effective amount" is intended an amount of the antiretroviral agent that is sufficient to decrease the effects of HIV infection, or an amount that is sufficient to favorably influence the pharmacokinetic profile of one or more of the other antiretroviral agents used in the HAART protocol. By "favorably influence" is intended that the antiretroviral agent, when administered in a therapeutically effective amount, affects the metabolism of one or more of the other antiretroviral agents used in HAART, such that the bioavailability of the other agent or other agents is increased. This can allow for decreased dosage frequency of the antiretroviral agent or agents whose bioavailability is increased in this manner. Decrease in dosage frequency can be advantageous for antiretroviral agents having undesirable side effects when administered in the absence of the antiretroviral agent that increases their bioavailability. The therapeutically effective dose of an antiretroviral agent for purposes of having a favorable influence on the phannacokinetics of another antiretroviral agent used in the HAART protocol is typically lower than the amount to be administered to have a direct therapeutic effect on HIV, such as inhibition of HIV replication. When used in this manner, an antiretroviral agent that has undesirable adverse effects at the full dosage required for therapeutic effectiveness against HIV replication can provide a therapeutic benefit a lower doses with fewer adverse side affects.

Thus, in one embodiment, an antiretroviral agent, when administered in a therapeutically effective amount to an HIV-infected subject, decreases the effects of HIV infection by, for example, inhibiting replication of HIV, thereby decreasing viral load in the subject undergoing antiretroviral therapy. In another embodiment, an antiretroviral agent, when administered in a therapeutically effective amount to an HIV-infected subject, favorably influences the pharmacokinetics of one or more of the other antiretroviral agents used in the HAART protocol.

For example, the protease inhibitor ritonavir when administered at full doses is a potent inhibitor of HIV in serum-and lymph nodes. When administered for these purposes, adverse reactions are common, such as gastrointestinal intolerance, hyperglycemia, insulin resistance, new onset or worsening diabetes, increased bleeding in hemophiliacs, circumoral and peripheral paresthesias, altered taste, and nausea and vomiting. Ritonavir can be administered at low doses (for example, 100 to 400 mg bid) with minimal intrinsic antiviral activity to increase the serum concentrations and decrease the dosage frequency of other protease inhibitors (see, Hsu et al. (1998) *Clin. Pharmacokinet.* 35:275). See, for example, the favorable influence of ritonavir on the protease inhibitor lopinavir (ABT-378) (Eron et al. (1999) *ICAAC* 39 addendum:18, Abstract LB-20).

Guidance as to dosages for any given antiretroviral agent is available in the art and includes administering commercially available agents at their recommended dosages. See, for example, *Medical Letter* 42(Jan. 10, 2000):1–6, herein incorporated by reference. Thus, for example, IDV can be administered at a dosage of about 800 mg, three times a day; D4T can be administered at a dosage of about 30–40 mg, twice a day; and Nelfinavir can be administered at a dosage of about 1250 mg, twice a day, or 750 mg three times a day. These agents are generally administered in oral formulations, though any suitable means of administration known in the art may be utilized for their delivery.

For purposes of the present invention, HAART is administered to an HIV-infected subject to effectively reduce the pool of actively replicating virus to an undetectable amount in plasma samples collected from the subject. By "undetectable amount" in the plasma is intended the amount of actively replicating HIV is less than about 500 RNA molecules/ml, preferably less than about 400 RNA molecules/ml, more preferably less than about 300 RNA molecules/ml, still more preferably less than about 200 RNA molecules/ml, even more preferably less than about 100 RNA molecules/ml, most preferably less than about 50 RNA molecules/ml. Any method known to those skilled in the art may be utilized to measure viral load in the plasma, including the methods described elsewhere herein. Thus, for example, plasma viral load can be determined using a branched chain DNA assay (bDNA), which has a lower limit of detection (LLD) of 50 HIV RNA molecules/ml (see Jacobson et al. (1996) *Proc. Natl. Acad. Sci. USA* 93:10405–10410; herein incorporated by reference). When an undetectable amount of replicating virus is present in a plasma sample obtained from an HIV-infected subject, plasma viral RNA is said to be "undetectable" in the subject.

In accordance with methods of the present invention, HIV-infected subjects are administered HAART for at least one cycle of an intermittent dosing regimen in combination with IL-2 therapy as defined elsewhere herein. By "intermittent dosing regimen" is intended a dosing regimen that comprises administering HAART to an HIV-infected subject for a time period sufficient to decrease plasma viral RNA to an undetectable amount, as previously defined, and then discontinuing administration of HAART until plasma viral RNA reaches an acceptable threshold level in the subject. By "acceptable threshold level" is intended a detectable amount of plasma viral RNA of at least about 200 RNA molecules/ml, preferably at least about 500 RNA molecules/ml, more preferably at least about 1,000 RNA molecules/ml, even more preferably at least about 5,000 RNA molecules/ml, most preferably at least about 10,000 RNA molecules/ml. When plasma viral RNA reaches an acceptable threshold level, a subsequent intermittent HAART dosing regimen is reinstated.

For example, in one embodiment, the HIV-infected subject undergoing IL-2 therapy as noted herein is administered HAART until plasma viral load is decreased to an undetectable level. HAART is then discontinued until plasma viral load reaches at least about 5,000 RNA molecules/ml, preferably at least about 10,000 molecules/ml, at which time HAART is reinstated until plasma viral load is once again decreased to an undetectable level.

The length of time HAART is administered to achieve an undetectable amount of actively replicating virus in the plasma, as well as the length of time to viral rebound following discontinuance of HAART, is a function of several factors, including, but not limited to, the severity of the disease, the combination and dosage of antiretroviral agents administered for purposes of HAART, and a patient's tolerance of HAART combined with IL-2 therapy, particularly with respect to side effects and adherence to protocol. Generally, in patients receiving cycles of intermittent HAART combined with IL-2 therapy, plasma viral load should be undetectable for at least about 1 week, preferably at least about 2 weeks, more preferably at least about 3 weeks, even more preferably at least about 4 weeks prior to discontinuance of HAART. Similarly, following discontinuance of HAART, an HIV-infected subject undergoing combined treatment with IL-2 therapy in accordance with methods of the present invention should have a plasma viral load that reaches the acceptable threshold level during at least two consecutive determinations, each of which is taken about one week apart, preferably taken about 10 days apart, more preferably taken about two weeks apart, prior to reinstating HAART. Monitoring of plasma viral RNA levels during time periods off of HAART therapy, such as with weekly or biweekly measurements, will ensure that the reconstituted immune system supported by IL-2 therapy has sufficient time to respond to the initial burst of viral replication that follows discontinuance of HAART, thereby preventing premature reinstatement of HAART.

As previously noted, HIV-infected subjects undergoing treatment with at least one cycle of an intermittent dosing regimen of HAART are concurrently undergoing treatment with IL-2 therapy. By "IL-2 therapy" is intended administration of IL-2 or variant thereof to a subject, where such administration provides a baseline level of IL-2 or variant thereof within that subject throughout each cycle of an intermittent dosing regimen of HAART. By "baseline level" of IL-2 or variant thereof is intended an amount of this agent that is sufficient to stimulate the immune system, thereby providing for immune reconstitution in the treated patient in the presence or absence of HAART administration. Immune reconstitution restores immune function and thus immune responsiveness in the patient. Restoration of immune function can be manifested by, for example, an increase in helper/inducer T-cell function, including an increased level of CD4+ cells, restoration of lymphocyte function, and/or an increase in the expression of IL-2 receptors.

IL-2 therapy comprises administering a pharmaceutical composition comprising a therapeutically effective amount or dose of IL-2 or variant thereof to an HIV-infected subject according to a particular dosing regimen throughout each cycle of an intermittent dosing regimen with HAART. Thus, within any given cycle, IL-2 is administered during administration of HAART and following discontinuance of HAART. For purposes of the present invention, a therapeutically effective amount or dose of IL-2 or variant thereof is an amount of IL-2 or variant thereof that, when administered according to a dosing regimen, is sufficient to restore immune function, and thus immune responsiveness, in the HIV-infected subject. The pharmaceutical composition comprising IL-2 or variant thereof can be administered using any acceptable method known in the art. Preferably the pharmaceutical composition comprising IL-2 or variant thereof is administered by way of injection, more preferably intravenous (IV) or subcutaneous (SC) injection, most preferably SC injection. What constitutes a therapeutically effective amount or dose of IL-2 or variant thereof is dependent upon the route of administration and the particular dosing regimen utilized. Additional factors that influence the mode of administration and the respective amount of IL-2 (or variant thereof) administered in combination with intermittent HAART include, but are not limited to, the severity of the HIV infection, the history of the disease, and the age, height, weight, health, and physical condition of the individual undergoing therapy. One of skill in the art could readily determine the amount of IL-2 or variant thereof to be administered in combination with at least one cycle of an intermittent HAART dosing regimen to improve immunologic control of HIV given the description of the present invention.

For example, in one embodiment of the invention, IL-2 therapy is provided by daily administration of low doses of IL-2 or variant thereof. By "low-dose" is intended the therapeutically effective amount of IL-2 or variant thereof ranges from about 0.6 mIU/m$^2$ to about 3.5 mIU/m$^2$, preferably from about 0.7 mIU/m$^2$ to about 3.0 mIU/m$^2$, more preferably from about 0.9 mIU/m$^2$ to about 1.5 mIU/m$^2$, still more preferably from about 1.0 mIU/m$^2$ to about 1.3 mIU/m$^2$, most preferably about 1.20 mIU/m$^2$. Although such low doses may be administered with any acceptable route, preferably the IL-2 or variant thereof is administered subcutaneously. Providing IL-2 therapy in this manner minimizes toxicity responses normally associated with IL-2 therapy at higher doses or high-bolus IL-2 administration. Such toxicity responses include, but are not limited to, chronic fatigue, nausea, hypotension, fever, chills, weight gain, pruritis or rash, dyspnea, azotemia, confusion, thrombocytopenia, myocardial infarction, gastrointestinal toxicity, and vascular leak syndrome (see, for example, Allison et al. (1989) *J. Clin. Oncol.* 7(1):75–80; and Gisselbrecht et al. (1994) *Blood* 83(8):2081–2085).

In another embodiment of the invention, IL-2 therapy is provided by intermittent administration of intermediate doses of IL-2 or variant thereof. By "intermediate dose" of IL-2 is intended the therapeutically effective amount of IL-2 or variant thereof ranges from about 3.0 mIU per day to about 15.0 mIU per day, preferably from about 6.0 mIU per day to about 12.0 mIU per day, more preferably from about 8.0 mIU per day to about 10.0 mIU per day, most preferably is about 9.0 mIU per day. Although such intermediate doses may be administered by any acceptable route, preferably the IL-2 or variant thereof is administered subcutaneously. By "intermittent" administration is intended the intermediate doses of IL-2 or variant thereof are administered for a period of time, and then withheld for a period of time. Thus, in one embodiment of the invention, intermittent administration of intermediate doses of IL-2 comprises SC administration of a pharmaceutical composition comprising IL-2 or variant thereof for 5 days, once every 4 weeks, preferably for 5 days, once every 6 weeks, more preferably for 5 days, once every 8 weeks in combination with at least one cycle of an intermittent dosing regimen for HAART.

Thus, methods of the invention comprise administering to an HIV-infected patient at least one cycle of an intermittent dosing regimen of HAART in combination with IL-2 therapy. IL-2 therapy provides a baseline level of this agent within the patient such that an effective immune defense can be mounted against actively replicating HIV in the absence of antiretroviral agents. When HAART is discontinued, these patients, who are immune reconstituted, have increased anti-viral reactivity that is manifested by an increase in CD8+ T cells, more specifically HIV antigen-specific CD8+cells. Proliferative expansion of CD8+ T cells, particularly HIV antigen-specific CD8+ T cells, effectively leads to a subsequent decline in viral load, such that immunological containment of replicating virus is achieved.

Methods of the present invention are beneficial with respect to treatment and/or management of HIV in an HIV-infected subject, particularly subjects with primary infection and those with chronic infection, so long as disease progression has not resulted in permanent loss of HIV-specific immunity. The degree of immunological containment achieved by any given patient is a function of their disease progression, history of the disease, and prior HIV treatment. Generally, HIV-infected subjects receiving at least one A cycle of intermittent HAART and IL-2 therapy in accordance with the methods of the present invention exhibit immunological containment of the virus in the absence of additional antiretroviral agents for a time period that is at least about 10%, preferably at least about 20%, more preferably at least about 25%, 30%, 35%, 40%, 45%, even at least about 50% longer than for a patient receiving intermittent HAART or IL-therapy alone.

Efficacy of the methods of the present invention and any adverse side effects can be monitored throughout the treatment of a subject using any of the methods available in the art, including those described in the examples below. A subject's vital signs, renal and liver function, glucose levels, etc., can be measured at predetermined time intervals. Activation of T cells can be assessed by IL-2 receptor expression. Blood samples can be analyzed for HIV using any protocol known to those skilled in the art. Polymerase chain reaction (PCR) can be used to determine the presence of HIV nucleic acid in biological samples. PBMCs can be collected from a subject at specific intervals, such as, for example, weekly or biweekly, and tested for infectious HIV by co-culturing with noninfected CD4+ cells. Infection of previously uninfected cells would be indicative of the presence of infectious HIV in the subject. These methods of detection could additionally be used to determine the presence of replicating HIV in lymph node samples obtained from a subject undergoing treatment in accordance with the methods of the invention. For example, the presence of replicating HIV in plasma can be determined using a branched chain DNA assay (bDNA), which has a lower limit of detection (LLD) of 50 HIV RNA molecules/ml (see Jacobson et al. (1996) *Proc. Natl. Acad. Sci. USA* 93:10405–10410; herein incorporated by reference). The presence of replicating HIV in lymph nodes can be determined using, for example, a co-culture assay (Chun (1999) *Nature* 401:874–875, herein incorporated by reference).

The term "IL-2" as used herein refers to a lymphokine that is produced by normal peripheral blood lymphocytes and is present in the body at low concentrations. IL-2 was first described by Morgan et al. (1976) *Science* 193:1007–1008 and originally called T cell growth factor because of its ability to induce proliferation of stimulated T lymphocytes. It is a protein with a reported molecular weight in the range of 13,000 to 17,000 (Gillis and Watson (1980) *J. Exp. Med.* 159:1709) and has an isoelectric point in the range of 6–8.5.

The IL-2 present in the pharmaceutical compositions described herein for use in the methods of the invention may be native or obtained by recombinant techniques, and may be from any source, including mammalian sources such as, e.g., mouse, rat, rabbit, primate, pig, and human. Preferably such polypeptides are derived from a human source, and more preferably are recombinant, human proteins from microbial hosts.

The pharmaceutical compositions useful in the methods of the invention may comprise biologically active variants of IL-2. Such variants should retain the desired biological activity of the native polypeptide such that the pharmaceutical composition comprising the variant polypeptide has the same therapeutic effect as the pharmaceutical composition comprising the native polypeptide when administered to a subject. That is, the variant polypeptide will serve as a therapeutically active component in the pharmaceutical composition in a manner similar to that observed for the native polypeptide. Methods are available in the art for determining whether a variant polypeptide retains the desired biological activity, and hence serves as a therapeutically active component in the pharmaceutical composition. Biological activity can be measured using assays specifically designed for measuring activity of the native polypeptide or protein, including assays described in the present invention. Additionally, antibodies raised against a biologically active native polypeptide can be tested for their ability to bind to the variant polypeptide, where effective binding is indicative of a polypeptide having a confirmation similar to that of the native polypeptide.

Suitable biologically active variants of native or naturally occurring IL-2 can be fragments, analogues, and derivatives of that polypeptide. By "fragment" is intended a polypeptide consisting of only a part of the intact polypeptide sequence and structure, and can be a C-terminal deletion or N-terminal deletion of the native polypeptide. By "analogue" is intended an analogue of either the native polypeptide or of a fragment of the native polypeptide, where the analogue comprises a native polypeptide sequence and structure having one or more amino acid substitutions, insertions, or deletions. "Muteins", such as those described herein, and peptides having one or more peptoids (peptide mimics) are also encompassed by the term analogue (see International Publication No. WO 91/04282). By "derivative" is intended any suitable modification of the native polypeptide of interest, of a fragment of the native polypeptide, or of their respective analogues, such as glycosylation, phosphorylation, polymer conjugation (such as with polyethylene glycol), or other addition of foreign moieties, so long as the desired biological activity of the native polypeptide is retained. Methods for making polypeptide fragments, analogues, and derivatives are generally available in the art.

For example, amino acid sequence variants of the polypeptide can be prepared by mutations in the cloned DNA sequence encoding the native polypeptide of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor Laboratory Press, Plainview, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇌Ala, Val⇌Ile⇌Leu, Asp⇌Glu, Lys⇌Arg, Asn⇌Gln, and Phe⇌Trp⇌Tyr.

In constructing variants of the IL-2 polypeptide of interest, modifications are made such that variants continue to possess the desired activity. Obviously, any mutations made in the DNA encoding the variant polypeptide must not place the sequence out of reading frame and preferably will not create complementary regions that could produce secondary mRNA structure. See EP Patent Application Publication No. 75,444.

Biologically active variants of IL-2 will generally have at least about 70%, preferably at least about 80%, more preferably at least about 90% to 95% or more, and most preferably at least about 98%, 99% or more amino acid sequence identity to the amino acid sequence of the reference IL-2 polypeptide molecule, such as native human IL-2, which serves as the basis for comparison. A biologically active variant of a native IL-2 polypeptide of interest may differ from the native polypeptide by as few as 1–15 amino acids, as few as 1–10, such as 6–10, as few as 5, as few as 4, 3, 2, or even 1 amino acid residue. By "sequence identity" is intended the same amino acid residues are found within the variant polypeptide and the polypeptide molecule that serves as a reference when a specified, contiguous segment of the amino acid sequence of the variants is aligned and compared to the amino acid sequence of the reference molecule. The percentage sequence identity between two amino acid sequences is calculated by determining the number of positions at which the identical amino acid residue occurs in both sequences to yield the number of matched positions, dividing the number of matched positions by the total number of positions in the segment undergoing comparison to the reference molecule, and multiplying the result by 100 to yield the percentage of sequence identity.

For purposes of optimal alignment of the two sequences, the contiguous segment of the amino acid sequence of the variants may have additional amino acid residues or deleted amino acid residues with respect to the amino acid sequence of the reference molecule. The contiguous segment used for comparison to the reference amino acid sequence will comprise at least twenty (20) contiguous amino acid residues, and may be 30, 40, 50, 100, or more residues. Corrections for increased sequence identity associated with inclusion of gaps in the variants' amino acid sequence can be made by assigning gap penalties. Methods of sequence alignment are well known in the art for both amino acid sequences and for the nucleotide sequences encoding amino acid sequences.

Thus, the determination of percent identity between any two sequences can be accomplished using a mathematical algorithm. One preferred, non-limiting example of a mathematical algorithm utilized for the comparison of sequences is the algorithm of Myers and Miller (1988) *CABIOS* 4:11–17. Such an algorithm is utilized in the ALIGN program (version 2.0), which is part of the GCG sequence alignment software package. A PAM120 weight residue table, a gap length penalty of 12, and a gap penalty of 4 can be used with the ALIGN program when comparing amino acid sequences. Another preferred, nonlimiting example of a mathematical algorithm for use in comparing two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to a nucleotide sequence encoding the polypeptide of interest. BLAST protein searches can be performed with the XBLAST program, score=50, wordlength=3, to obtain amino acid sequences homologous to the polypeptide of interest. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See www.ncbi.nlm.nih.gov. Also see the ALIGN program (Dayhoff (1978) in *Atlas of Protein Sequence and Structure* 5:Suppl. 3 (National Biomedical Research Foundation, Washington, D.C.) and programs in the Wisconsin Sequence Analysis Package, Version 8 (available from Genetics Computer Group, Madison, Wis.), for example, the GAP program, where default parameters of the programs are utilized.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Myers and Miller (1988) *Computer Applic. Biol. Sci.* 4:11–17.

For purposes of the present invention, preferably percent sequence identity between the variant IL-2 polypeptide and the reference IL-2 polypeptide, such as native or naturally occurring IL-2, more particularly native human IL-2, is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) *Adv. Appl. Math.* 2:482–489.

The precise chemical structure of a polypeptide having IL-2 activity depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of polypeptides having IL-2 activity as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an IL-2 polypeptide used herein so long as the IL-2 activity of the polypeptide is not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy activity do not remove the polypeptide sequence from the definition of IL-2 polypeptides of interest as used herein.

The art provides substantial guidance regarding the preparation and use of polypeptide variants. In preparing the IL-2 variants, one of skill in the art can readily determine which modifications to the native protein nucleotide or amino acid sequence will result in a variant that is suitable for use as a therapeutically active component of a pharmaceutical composition used in the methods of the present invention.

The IL-2 or variants thereof for use in the methods of the present invention may be from any source, but preferably is recombinant IL-2. By "recombinant IL-2" is intended interleukin-2 that has comparable biological activity to native-sequence IL-2 and that has been prepared by recombinant DNA techniques as described, for example, by Taniguchi et al. (1983) *Nature* 302:305–310 and Devos (1983) *Nucleic Acids Research* 11:4307–4323 or mutationally altered IL-2 as described by Wang et al. (1984) *Science* 224:1431–1433. In general, the gene coding for IL-2 is cloned and then expressed in transformed organisms, preferably a microorganism, and most preferably *E. coli*, as described herein. The host organism expresses the foreign gene to produce IL-2 under expression conditions. Synthetic recombinant IL-2 can also be made in eukaryotes, such as yeast or human cells. Processes for growing, harvesting, disrupting, or extracting the IL-2 from cells are substantially described in, for example, U.S. Pat. Nos. 4,604,377; 4,738,927; 4,656,132; 4,569,790; 4,748,234; 4,530,787; 4,572,798; 4,748,234; and 4,931,543, herein incorporated by reference in their entireties.

For examples of variant IL-2 proteins, see European Patent Application No. 136,489; European Patent Application No. 83101035.0 filed Feb. 3, 1983 (published Oct. 19, 1983 under Publication No. 91539); European Patent Application No. 82307036.2, filed Dec. 22, 1982 (published Sep. 14, 1983 under No. 88195); the recombinant IL-2 muteins described in European Patent Application No. 83306221.9, filed Oct. 13, 1983 (published May 30, 1984 under No. 109748), which is the equivalent to Belgian Patent No. 893,016, commonly owned U.S. Pat. No. 4,518,584; the muteins described in U.S. Pat. No. 4,752,585 and WO 99/60128; and the IL-2 mutein (des-alanyl-1, serine-125 human interleukin-2) used in the examples herein and described in U.S. Pat. No. 4,931,543, as well as the other IL-2 muteins described in this U.S. patent; all of which are herein incorporated by reference. Additionally, IL-2 can be modified with polyethylene glycol to provide enhanced solubility and an altered pharmokinetic profile (see U.S. Pat. No. 4,766,106, hereby incorporated by reference in its entirety).

Any pharmaceutical composition comprising IL-2 as the therapeutically active component can be used in the methods of the invention. Such pharmaceutical compositions are known in the art and include, but are not limited to, those disclosed in U.S. Pat. Nos. 4,745,180; 4,766,106; 4,816,440; 4,894,226; 4,931,544; and 5,078,997; herein incorporated by reference. Thus liquid, lyophilized, or spray-dried compositions comprising IL-2 or variants thereof that are known in the art may be prepared as an aqueous or nonaqueous solution or suspension for subsequent administration to a subject in accordance with the methods of the invention. Each of these compositions will comprise IL-2 or variants thereof as a therapeutically or prophylactically active component. By "therapeutically or prophylactically active component" is intended the IL-2 or variants thereof is specifically incorporated into the composition to bring about a desired therapeutic or prophylactic response with regard to treatment or prevention of a disease or condition within a subject when the pharmaceutical composition is administered to that subject. Preferably the pharmaceutical compositions comprise appropriate stabilizing agents, bulking agents, or both to minimize problems associated with loss of protein stability and biological activity during preparation and storage.

In preferred embodiments of the invention, the IL-2 containing pharmaceutical compositions useful in the methods of the invention are compositions comprising stabilized monomeric IL-2 or variants thereof, compositions comprising multimeric IL-2 or variants thereof, and compositions comprising stabilized lyophilized or spray-dried IL-2 or variants thereof.

Pharmaceutical compositions comprising stabilized monomeric IL-2 or variants thereof are disclosed in the copending PCT application entitled "*Stabilized Liquid 3Polypeptide-Containing Pharmaceutical Compositions*," assigned PCT No. PCT/US00/27156, filed Oct. 3, 2000, the disclosure of which is herein incorporated by reference. By "monomeric" IL-2 is intended the protein molecules are present substantially in their monomer form, not in an aggregated form, in the pharmaceutical compositions described herein. Hence covalent or hydrophobic oligomers or aggregates of IL-2 are not present. Briefly, the IL-2 or variants thereof in these liquid compositions is formulated with an amount of an amino acid base sufficient to decrease aggregate formation of IL-2 or variants thereof during storage. The amino acid base is an amino acid or a combination of amino acids, where any given amino acid is present either in its free base form or in its salt form. Preferred amino acids are selected from the group consisting of arginine, lysine, aspartic acid, and glutamic acid. These compositions further comprise a buffering agent to maintain pH of the liquid compositions within an acceptable range for stability of IL-2 or variants thereof, where the buffering agent is an acid substantially free of its salt form, an acid in its salt form, or a mixture of an acid and its salt form. Preferably the acid is selected from the group consisting of succinic acid, citric acid, phosphoric acid, and glutamic acid. Such compositions are referred to herein as stabilized monomeric IL-2 pharmaceutical compositions.

The amino acid base in these compositions serves to stabilize the IL-2 or variants thereof against aggregate formation during storage of the liquid pharmaceutical composition, while use of an acid substantially free of its salt form, an acid in its salt form, or a mixture of an acid and its salt form as the buffering agent results in a liquid composition having an osmolarity that is nearly isotonic. The liquid pharmaceutical composition may additionally incorporate other stabilizing agents, more particularly methionine, a nonionic surfactant such as polysorbate 80, and EDTA, to further increase stability of the polypeptide. Such liquid pharmaceutical compositions are said to be stabilized, as addition of amino acid base in combination with an acid substantially free of its salt form, an acid in its salt form, or a mixture of an acid and its salt form, results in the compositions having increased storage stability relative to liquid pharmaceutical compositions formulated in the absence of the combination of these two components.

These liquid pharmaceutical compositions comprising stabilized monomeric IL-2 or variants thereof may either be used in an aqueous liquid form, or stored for later use in a frozen state, or in a dried form for later reconstitution into a liquid form or other form suitable for administration to a subject in accordance with the methods of present invention. By "dried form" is intended the liquid pharmaceutical composition or formulation is dried either by freeze drying (i.e., lyophilization; see, for example, Williams and Polli (1984) *J. Parenteral Sci. Technol.* 38:48–59), spray drying (see Masters (1991) in *Spray-Drying Handbook* (5th ed; Longman Scientific and Technical, Essex, U.K.), pp. 491–676; Broadhead et al. (1992) *Drug Devel. Ind. Pharm.* 18:1169–1206; and Mumenthaler et al. (1994) *Pharm. Res.* 11:12–20), or air drying (Carpenter and Crowe (1988) *Cryobiology* 25:459–470; and Roser (1991) *Biopharm.* 4:47–53).

Examples of pharmaceutical compositions comprising multimeric IL-2 or variants thereof are disclosed in commonly owned U.S. Pat. No. 4,604,377, the disclosure of which is herein incorporated by reference. By "multimeric" is intended the protein molecules are present in the pharmaceutical composition in a microaggregated form having an average molecular association of 10–50 molecules. These multimers are present as loosely bound, physically-associated IL-2 molecules. A lyophilized form of these compositions is available commercially under the tradename Proleukin (Chiron Corporation, Emeryville, Calif.). The lyophilized formulations disclosed in this reference comprise selectively oxidized, microbially produced recombinant IL-2 in which the recombinant IL-2 is admixed with a water soluble carrier such as mannitol that provides bulk, and a sufficient amount of sodium dodecyl sulfate to ensure the solubility of the recombinant IL-2 in water. These compositions are suitable for reconstitution in aqueous injections for parenteral administration and are stable and well tolerated in human patients. When reconstituted, the IL-2 or variants thereof retains its multimeric state. Such lyophilized or liquid compositions comprising multimeric IL-2 or variants thereof are encompassed by the methods of the present invention. Such compositions are referred to herein as multimeric IL-2 pharmaceutical compositions.

The methods of the present invention may also use stabilized lyophilized or spraydried pharmaceutical compositions comprising IL-2 or variants thereof, which may be reconstituted into a liquid or other suitable form for administration in accordance with methods of the invention. Such pharmaceutical compositions are disclosed in the copending application entitled "Methods for Pulmonary Delivery of Interleukin-2," U.S. Provisional Application Ser. No. 60/173,922, filed Dec. 30, 1999, herein incorporated by reference. These compositions may further comprise at least one bulking agent, at least one agent in an amount sufficient to stabilize the protein during the drying process, or both. By "stabilized" is intended the IL-2 protein or variants thereof retains its monomeric or multimeric form as well as its other key properties of quality, purity, and potency following lyophilization or spray-drying to obtain the solid or dry powder form of the composition. In these compositions, preferred carrier materials for use as a bulking agent include glycine, mannitol, alanine, valine, or any combination thereof, most preferably glycine. The bulking agent is present in the formulation in the range of 0% to about 10% (w/v), depending upon the agent used. Preferred carrier materials for use as a stabilizing agent include any sugar or sugar alcohol or any amino acid. Preferred sugars include sucrose, trehalose, raffinose, stachyose, sorbitol, glucose, lactose, dextrose or any combination thereof, preferably sucrose. When the stabilizing agent is a sugar, it is present in the range of about 0% to about 9.0% (w/v), preferably about 0.5% to about 5.0%, more preferably about 1.0% to about 3.0%, most preferably about 1.0%. When the stabilizing agent is an amino acid, it is present in the range of about 0% to about 1.0% (w/v), preferably about 0.3% to about 0.7%, most preferably about 0.5%. These stabilized lyophilized or spray-dried compositions may optionally comprise methionine, ethylenediaminetetracetic acid (EDTA) or one of its salts such as disodium EDTA or other chelating agent, which protect the IL-2 or variants thereof against methionine oxidation. Use of these agents in this manner is described in copending U.S. Provisional Application Ser. No. 60/157696, herein incorporated by reference. The stabilized lyophilized or spray-dried compositions may be formulated using a buffering agent, which maintains the pH of the pharmaceutical composition within an acceptable range, preferably between about pH 4.0 to about pH 8.5, when in a liquid phase, such as during the formulation process or following reconstitution of the dried form of the composition. Buffers are chosen such that they are compatible with the drying process and do not affect the quality, purity, potency, and stability of the protein during processing and upon storage.

The previously described stabilized monomeric, multimeric, and stabilized lyophilized or spray-dried IL-2 pharmaceutical compositions represent suitable compositions for use in the methods of the invention. However, any pharmaceutical composition comprising IL-2 or variant thereof as a therapeutically active component is encompassed by the methods of the invention.

The following examples are offered by way of illustration and not by way of limitation.

Experimental

HIV disease is characterized by an impairment of antigen-induced IL-2 production, particularly in subjects with more advanced disease. Exogenous IL-2, in association with HIV antigen, should enhance expansion of HIV-specific CTLs and augment the effector function of these cells, thus leading to tighter immunologic control of HIV. Prolonged administration of IL-2 might actually promote HIV-specific cellular immunity.

A small uncontrolled trial showed that discontinuation of HAART in 9 subjects with HIV infection receiving low-dose daily subcutaneous IL-2 was followed by a transient surge in viremia commencing a mean of about 19 days after discontinuation of HAART, and peaking roughly two weeks after this (Emert et al. (2000) "Structured antiviral treatment interruption followed by daily low dose interleukin 2 (IL-2) reveals immune response to HIV," Abstract, AIDS 2000 XIII International AIDS Conference, Durban, Jul. 9–14, 2000). The levels of plasma virus subsequently declined in concert with a rise in CD8+ T cells. By 6 weeks after the onset of viremia, the mean virus concentration had decreased to less than 10% of the peak concentration. These data further support a possible role for IL-2 in the immunologic control of HIV infection.

An HIV-specific CTL response is important in subduing HIV infection. There has been difficulty in constructing vaccines that consistently elicit potent and broad HIV-specific CTL responses. A solution might lie in therapeutic "auto-immunization." Through controlled exposure to bursts of HIV during antiviral "drug holidays," interruptions of HAART may fortify the HIV-specific memory CTL response and, thereby, promote more lasting immunologic control of HIV infection. IL-2 might further strengthen this HIV-specific CTL response and enhance the likelihood of attaining the goal of long-term immunologic containment of infection. Even if permanent immunologic containment is not possible, a decrease in exposure to HAART with antiretroviral "drug holidays" would be welcomed by patients, for whom HAART pill burdens can be significant and in whom HAART has clearly demonstrated an ability to produce unwanted long-term side effects.

The following controlled study is undertaken to demonstrate the effect of intermittent courses of potent antiviral therapy (HAART), in conjunction with subcutaneous (SC) IL-2, on plasma and tissue viral burden as well as HIV-specific immunity.

EXAMPLE 1

Initial Clinical Trial

The IL-2 formulation used in this study is manufactured by Chiron Corporation of Emeryville, Calif., under the tradename Proleukin. The IL-2 in this formulation is a recombinantly produced human IL-2 mutein, called aldesleukin, which differs from the native human IL-2 sequence in having the initial alanine residue eliminated and the cysteine residue at position 125 replaced by a serine residue (referred to as des-alanyl-1, serine-125 human interleukin-2). This IL-2 mutein is expressed from *E. coli*, and subsequently purified by diafiltration and cation exchange chromatography as described in U.S. Pat. No. 4,931,543. The IL-2 formulation marketed as Proleukin is supplied as a sterile, white to off-white preservative-free lyophilized powder in vials containing 1.3 mg of protein (22 MIU).

One hundred twenty subjects infected with HIV-1 with at least 500 CD4+ T cells/mm$^3$, and undetectable viremia using a third generation bDNA assay are randomized to one of three arms:

A. continued HAART×eight months
B. intermittent HAART×eight months
C. intermittent HAART+daily low-dose SC IL-2, 1.2 MIU/m$^2$×eight months Plasma viral load will be monitored weekly on study. In groups B and C, HAART will stopped on study day one. HAART will be resumed if plasma viral load climbs to greater than 10,000 copies/ml at two consecutive determinations and/or there is evidence of clinical disease progression that, in the opinion of the investigator, mandates the resumption of antiviral therapy. CD4+ T-cell counts will be monitored. CD4+T-cell counts of less than 350 cells/mm$^3$ will trigger the resumption of antiviral therapy. Patients in this last category will be removed from trial and replaced.

If, in response to viral rebound, HAART is resumed for a subject in group B or C, it will be stopped after 12 weeks of administration if viral load has become undetectable by that time. If viral load remains detectable after a twelve week resumption of HAART, HAART will continue until virus is undetectable. The algorithm for determining when to resume HAART after a second interruption of antiretroviral therapy will be identical to that used to determine when to initiate HAART after the first (i.e., day one) interruption. There will be no more than two interruptions of HAART in groups B and C during the first eight months on study.

After eight months of study participation, those subjects with undetectable viremia on HAART (UVHAART) will stop antiretrovirals. It is expected that approximately 80% of enrolled subjects will fall into this category. These subjects will be followed for four additional months on study. Antiretrovirals may be resumed at the discretion of the investigator if viral load climbs to at least 10,000 copies/ml at two consecutive determinations or if CD4+ T-cell counts fall below 350 cells/mm$^3$.

At the end of eight months, subjects who are not receiving HAART (NOHAART) and those with detectable virus on HAART (DVHAART) will be followed observationally. Data regarding antiretroviral therapy and viral load will be collected on these subjects, but decisions regarding antiretroviral therapy will fall under the purview of the investigator.

Selection of antiretroviral agents will be the responsibility of the investigator but, in no instance will a subject be treated with a regimen that does not constitute highly active antiretroviral therapy (HAART), defined as use of three or more antiretroviral agents, or dual protease-inhibitor therapy. Agents with immunomodulatory effects will not be permitted on trial. Routine (i.e., non-urgent) vaccinations will not be permitted on trial.

Major eligibility criteria include: 1) undetectable pVL by third generation bDNA assay at two determinations at least one week apart within one month of study entry; 2) stable antiretroviral therapy for three months; 3) CD4+ T-cell count of at least 500 cells/mm$^3$; and 4) negative serum or urine pregnancy test.

Efficacy Variables

Primary: Time to virologic rebound among subjects with undetectable viral load on HAART at month eight.

Secondary:
Proportion of subjects with undetectable pVL at months eight and twelve
Kinetics of viral rebound following month eight HAART interruption
Duration of time on HAART (on study)
Proportion of subjects on HAART at months eight and twelve
Replication-competent HIV in resting CD4+ cells using a co-culture assay (months eight and twelve)
Replication-competent HIV in lymph node cells at months eight and twelve
HIV-specific CTL activity at months eight and twelve
HIV-specific CD4+ proliferative response at months eight and twelve
CTL CD3 zeta expression at months eight and twelve
Mean change from baseline in CD4+ cell count at month 12

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

That which is claimed:

1. A method of promoting immunologic control of human immunodeficiency virus (HIV) in an HIV-infected subject, said method comprising administering to said subject highly active antiretroviral therapy (HAART) for at least one cycle of an intermittent dosing regimen in combination with administration of a pharmaceutical composition comprising a therapeutically effective amount of interleukin-2 (IL-2) or variant thereof, said variant thereof having at least 70% sequence identity to said IL-2, wherein said administration provides a baseline level of said IL-2 within said subject.

2. The method of claim 1, wherein said HAART comprises daily administration of at least three antiretroviral agents, wherein a therapeutically effective amount of each of said antiretroviral agents is administered.

3. The method of claim 2, wherein said antiretroviral agents are selected from the group consisting of reverse transcriptase inhibitors and protease inhibitors.

4. The method of claim 3, wherein said reverse transcriptase inhibitors are selected from the group consisting of dideoxyinosine (ddI), zidovudine (AZT), zalcitabine (ddC), lamivudine (3TC), stavudine (D4T), abacavir, delavirdine, efavirenz, and nevirapine.

5. The method of claim 3, wherein said protease inhibitors are selected from the group consisting of Indinavir (IDV), Amprenavir, saquinavir, ritonavir, ABT-378, nelfinavir, and GW141.

6. The method of claim 1, wherein said intermittent dosing regimen for HAART comprises administering HAART to said subject until plasma viral RNA is undetectable in said subject, and then discontinuing administration of said HAART until plasma viral RNA reaches an acceptable threshold level in said subject.

7. The method of claim 6, wherein said plasma viral RNA is undetectable in said subject for at least about one month prior to discontinuing HAART, and wherein said acceptable threshold level of said plasma viral RNA is about 10,000 molecules/ml at two consecutive measurements taken about one week apart.

8. The method of claim 1, wherein said IL-2 or variant thereof is administered subcutaneously.

9. The method of claim 1, wherein said IL-2 or variant thereof is administered daily.

10. The method of claim 9, wherein said therapeutically effective amount of said IL-2 or variant thereof is in the range from about 0.6 mIU/M$^2$ to about 3.5 mIU/m$^2$.

11. The method of claim 10, wherein said therapeutically effective amount of said IL-2 or variant thereof is in the range from about 0.7 mIU/m$^2$ to about 3 mIU/m$^2$.

12. The method of claim 11, wherein said therapeutically effective amount of said IL-2 or variant thereof is about 1.20 mIU/m$^2$.

13. The method of claim 1, wherein said IL-2 or variant thereof is administered intermittently.

14. The method of claim 1, wherein said pharmaceutical composition comprising IL-2 or variant thereof is selected from the group consisting of a stabilized monomeric IL-2 pharmaceutical composition, a multimeric IL-2 pharmaceutical composition, a stabilized lyophilized IL-2 pharmaceutical composition, and a stabilized spray-dried IL-2 pharmaceutical composition.

15. The method of claim 14, wherein said IL-2 is recombinantly produced IL-2 having an amino acid sequence for human IL-2 or variant thereof, said variant thereof having at least 70% sequence identity with human IL-2.

16. The method of claim 15, wherein said variant thereof is des-alanyl-1, serine-125 human interleukin-2.

17. A method of treating a subject infected with human immunodeficiency virus (HIV), said method comprising administering to said subject highly active antiretroviral therapy (HAART) for at least one cycle of an intermittent dosing regimen in combination with administration of a pharmaceutical composition comprising a therapeutically effective amount of interleukin-2 (IL-2) or variant thereof, said variant thereof having at least 70% sequence identity with IL-2, wherein said administration provides a baseline level of said IL-2 within said subject.

18. The method of claim 17, wherein said HAART comprises daily administration of at least three antiretroviral agents, wherein a therapeutically effective amount of each of said antiretroviral agents is administered.

19. The method of claim 18, wherein said antiretroviral agents are selected from the group consisting of reverse transcriptase inhibitors and protease inhibitors.

20. The method of claim 19, wherein said reverse transcriptase inhibitors are selected from the group consisting of dideoxyinosine (ddI), zidovudine (AZT), zalcitabine (ddC), lamivudine (3TC), stavudine (D4T), abacavir, delavirdine, efavirenz, and nevirapine.

21. The method of claim 19, wherein said protease inhibitors are selected from the group consisting of Indinavir (IDV), Amprenavir, saquinavir, ritonavir, ABT-378, nelfinavir, and GW141.

22. The method of claim 17, wherein said intermittent dosing regimen for HAART comprises administering HAART to said subject until plasma viral RNA is undetectable in said subject, and then discontinuing administration of said HAART until plasma viral RNA reaches an acceptable threshold level in said subject.

23. The method of claim 22, wherein said plasma viral RNA is undetectable in said subject for at least about one month prior to discontinuing HAART, and wherein said acceptable threshold level of said plasma viral RNA is about 10,000 molecules/ml at two consecutive measurements taken about one week apart.

24. The method of claim 17, wherein said IL-2 or variant thereof is administered subcutaneously.

25. The method of claim 17, wherein said IL-2 or variant thereof is administered daily.

26. The method of claim 25, wherein said therapeutically effective amount of said IL-2 or variant thereof is in the range from about 0.6 mIU/m$^2$ to about 3.5 mIU/m$^2$.

27. The method of claim 26, wherein said therapeutically effective amount of IL-2 or variant thereof is in the range from about 0.7 mIU/m$^2$ to about 3 mIU/m$^2$.

28. The method of claim 27, wherein said therapeutically effective amount of said IL-2 or variant thereof is about 1.20 mIU/m$^2$.

29. The method of claim 17, wherein said IL-2 or variant thereof is administered intermittently.

30. The method of claim 17 wherein said pharmaceutical composition comprising IL-2 or variant thereof is selected from the group consisting of a stabilized monomeric IL-2 pharmaceutical composition, a multimeric IL-2 pharmaceutical composition, a stabilized lyophilized IL-2 pharmaceutical composition, and a stabilized spray-dried IL-2 pharmaceutical composition.

31. The method of claim 30, wherein said IL-2 is recombinantly produced IL-2 having an amino acid sequence for human IL-2 or variant thereof, said variant thereof having at least 70% sequence identity with human IL-2.

32. The method of claim 31, wherein said variant thereof is des-alanyl-1, serine-125 human interleukin-2.

33. A method of treating a subject infected with human immunodeficiency virus (HIV), said method comprising administering to said subject highly active antiretroviral therapy (HAART) for at least one cycle of an intermittent dosing regimen in combination with interleukin-2 (IL-2) therapy, wherein said IL-2 therapy comprises administering a pharmaceutical composition comprising a therapeutically effective amount of IL-2 or variant thereof throughout each cycle of said intermittent dosing regimen of HAART, said variant thereof having at least 70% sequence identity with said IL-2, wherein said administration provides a baseline level of said IL-2 within said subject, and wherein said intermittent dosing regimen for HAART comprises administering HAART to said subject until plasma viral RNA is undetectable in said subject for at least about one month prior to discontinuing HAART, and then discontinuing administration of said HAART until plasma viral RNA reaches at least about 10,000 molecules/ml at two consecutive measurements taken about one week apart.

34. The method of claim 33, wherein said IL-2 or variant thereof is administered daily by subcutaneous injection.

35. The method of claim 34, wherein said therapeutically effective amount of said IL-2 or variant thereof is in the range from about 0.2 mIU/m$^2$ to about 5 mIU/m$^2$.

36. The method of claim 35, wherein said therapeutically effective amount of IL-2 or variant thereof is in the range from about 0.5 mIU/m$^2$ to about 2 mIU/m$^2$.

37. The method of claim 36, wherein said therapeutically effective amount of said IL-2 or variant thereof is about 1.20 mIU/m$^2$.

* * * * *